United States Patent [19]

Getman et al.

[11] Patent Number: 5,025,021
[45] Date of Patent: Jun. 18, 1991

[54] 1,2-DIDEOXY-2-FLUORONOJIRIMYCIN AS GLYCOSIDASE INHIBITORS

[75] Inventors: Daniel P. Getman, St. Louis; Gary A. DeCrescenzo, St. Peters, both of Mo.

[73] Assignee: Monsanto Company, St. Louis, Mo.

[21] Appl. No.: 386,538

[22] Filed: Jul. 27, 1989

[51] Int. Cl.$^5$ ................. A61K 31/445; C07D 211/46; C07D 491/056
[52] U.S. Cl. .................... 514/302; 514/315; 514/328; 546/116; 546/219; 546/220; 546/242
[58] Field of Search ............. 546/116, 219, 220, 242; 514/302, 315, 328

[56] References Cited

U.S. PATENT DOCUMENTS 4,348,402 9/1982 Kinast et al. .................. 546/198

FOREIGN PATENT DOCUMENTS 3620645 7/1987 Fed. Rep. of Germany .

OTHER PUBLICATIONS

Minavu et al, J. Org. Chem., 41 1831 (1976).
David et al, Tetrahedron, 41, (4), 643 (1985).
Tsuda et al, Chem. Pharm. Bull., 31(5), 1612 (1983).
Boshagan et al, Carbohydrate Research, 164, 141 (1987).

*Primary Examiner*—Bernard I. Dentz
*Attorney, Agent, or Firm*—Charles E. Smith; James W. Williams, Jr.; James C. Bolding

[57] ABSTRACT

Novel compounds represented by the formula:

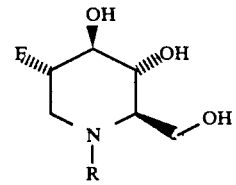

wherein R represents hydrogen, optionally substituted alkyl radicals having from 1 to about 10 carbon atoms, optionally substituted alkenyl radicals having from 1 to about 10 carbon atoms, optionally substituted aryl, alkaryl and aralkyl radicals having from about 6 to about 16 carbon atoms and optionally substituted acyl and acyloxy radicals having from about 1 to about 10 carbon atoms, manifest glycosidase inhibition activity.

19 Claims, No Drawings

1,2-DIDEOXY-2-FLUORONOJIRIMYCIN AS GLYCOSIDASE INHIBITORS

BACKGROUND OF THE INVENTION

1. Field of the Invention

This invention relates to novel piperidine derivatives which manifest glycosidase inhibition activity and to novel intermediates useful in the manufacture thereof. The present invention also relates to methods for preparing such derivatives and intermediates.

More particularly, the present invention relates to 5-fluoro analogs of 2-hydroxymethyl-3, 4,-dihydroxypiperidines, which are the ring nitrogen analogs of 1-deoxy-D-glucose and are generally referred to as 1-deoxynojirimycin (DNJ) analogs. More particularly, the present invention relates to 1,2-dideoxy-2-fluoronojirimycin and the corresponding N-derivatives; to intermediates useful in preparing such fluorinated analogs; to methods for preparing the intermediates beginning with 1-deoxynojirimycin as starting material; and to methods for preparing the 2-fluoro analogs utilizing such intermediates.

2. Related Art

1-Deoxynojirimycin is a known glucosidase inhibitor. See, for example, Truscheit et al., Ang. Chemie Int'l Ed., 20, 744 (1981). Fluoro analogs of Chemie Int glucose and glucose derivatives are also known. For example, see Withers et al, J.Amer. Chem. Soc., 109, 7530–31 (1987), and "Fluorinated Carbohydrates: Chemical and Biochemical Aspects; ACS Symposium Series 184," ed. N.F. Taylor, American Chemical Society (1988).

Kinast et al, DE3620645, disclose 2-amino-1-deoxynojirimycin derivatives which inhibit glucosidases. A cyclic stannylene intermediate of 1-deoxymannojirimycin is utilized to specifically functionalize the 3-hydroxy group.

Munava et al, J. Org. Chem., 41, 1832 (1976),. disclose a cyclic stannylene intermediate of glucose utilized to functionalize the 2-hydroxy group with a benzoyl group.

David et al, Tetrahedron, 41(4), 643 (1985) review utilization of stannylenes in carbohydrate chemistry.

SUMMARY OF THE INVENTION

The present invention is directed at 1,2-dideoxy-2-fluoronojirimycin, and the N-derivatives thereof. These compounds are prepared utilizing novel N-substituted-4,6-O-benzylidene-1,2-dideoxy-2-fluoronojirimycin intermediates, N-substituted-2,3-anhydro-4,6-O-benzylidene-1-deoxymannojirimycin intermediates, N-substituted-4,6-O-benzylidene-2-O-(sulfonyl ester)1-deoxynojirimycin intermediates and N-substituted2,3-O-(dialkylstannylene)-4,6-O-benzylidene-1-deoxynojirimycin intermediates which are then utilized to produce the subject compounds.

DETAILED DESCRIPTION OF THE INVENTION

The present invention resides in the discovery that novel 2-deoxy-2-fluoro analogs of 1-deoxynojirimycin and the N-derivatives thereof manifest glycosidase inhibition activity. The subject compounds can be represented by the formula:

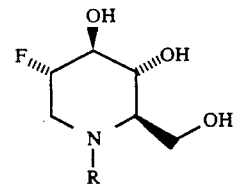

wherein R represents hydrogen, optionally substituted alkyl radicals having from 1 to about 10 carbon atoms, optionally substituted alkenyl radicals having from 1 to about 10 carbon atoms, optionally substituted aryl, alkaryl and aralkyl radicals having from about 6 to about 16 carbon atoms, and optionally substituted acyl and acyloxy radicals having from about 1 to about 10 carbon atoms. Accordingly, the present invention is directed to such novel analogs, to novel intermediates useful in the manufacture of such analogs, and to methods for preparing such novel intermediates and analogs.

These novel analogs and intermediates can be represented generically by the formula:

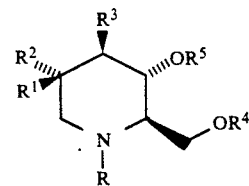

wherein R represents hydrogen, optionally substituted alkyl radicals having from 1 to about 10 carbon atoms, optionally substituted alkenyl radicals having from 1 to about 10 carbon atoms, optionally substituted aryl, alkaryl and aralkyl radicals having from about 6 to about 16 carbon atoms and optionally substituted acyl and acyloxy radicals having from about 1 to about 10 carbon atoms; $R^1$ represents hydrogen; $R^2$ represents hydrogen, fluorine, and sulfonyl esters represented by the following formula:

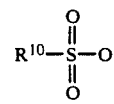

wherein $R^{10}$ represents optionally substituted alkyl radicals having from 1 to about 6 carbon atoms and optionally substituted aryl, aralkyl and alkaryl radicals; $R^3$ represents hydroxy or together with $R^2$ represents a cyclic stannylene derivative of the formula

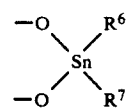

wherein $R^6$ and $R^7$ independently represent alkyl radicals having from 1 to about 10 carbon atoms, or together with $R^1$ represents an epoxide; provided that when $R^2$ is fluorine, $R^3$ is hydroxy; and when $R^2$ is hydrogen, $R^1$ and $R^3$ together form an epoxide; and $R^4$ and $R^5$ represent hydrogen and hydroxy protecting groups.

More particularly, the novel analogs can be represented by the formula:

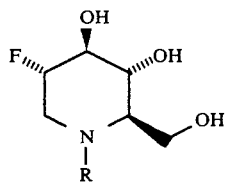

wherein R represents hydrogen, optionally substituted alkyl radicals having from 1 to about 10 carbon atoms, optionally substituted alkenyl radicals having from 1 to about 10 carbon atoms, optionally substituted aryl, alkaryl and aralkyl radicals having from about 6 to about 16 carbon atoms and optionally substituted acyl and acyloxy radicals having from about 2 to about 10 carbon atoms.

The N-substituted-4,6-O-protected-1,2-dideoxy-2-fluoronojirimycin intermediates can be represented by the formula:

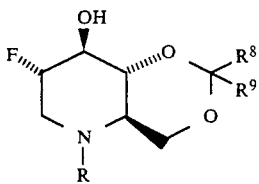

wherein R has the same meaning as set forth above and $R^8$ and $R^9$ independently represent hydrogen, substituted and unsubstituted alkyl radicals having from 1 to about 10 carbon atoms and substituted and unsubstituted aryl radicals.

The epoxide intermediates can be represented by the formula:

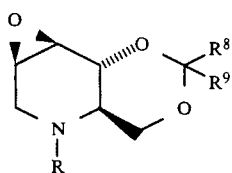

wherein R, $R^8$ and $R^9$ have the same meaning as set forth above.

The 2-substituted intermediates can be represented by the formula:

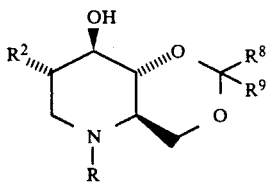

wherein R has the same meaning as set forth above; $R^2$ represents substituted and unsubstituted sulfonyl ester represented by the formula:

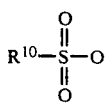

wherein $R^{10}$ represents optionally substituted alkyl radicals having from 1 to about 6 carbon atoms and optionally substituted aryl, aralkyl and alkaryl radicals; and $R^8$ and $R^9$ have the same meaning as set forth above.

The cyclic stannylene intermediates can be represented by the formula:

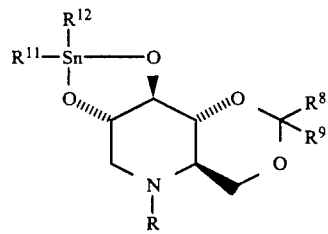

wherein R, $R^8$ and $R^9$ represent radicals as defined above; and $R^{11}$ and $R^{12}$ represent alkyl radicals having from 1 to about 10 carbon atoms.

The 1,2-dideoxy-2-fluoronojirimycin compound of the present invention can be prepared beginning with 1-deoxynojirimycin (hereinafter referred to as "DNJ"), which can be prepared by known procedures as disclosed in U.S. Pat. Nos. 4,220,782; 4,246,345; and 4,806,650. The corresponding N-alkyl derivatives can then be prepared according to known procedures. See, for example, U.S. Pat. Nos. 4,220,782; 4,266,025; 4,405,714; and 4,806,650.

Starting with DNJ, the N-alkyl group can first be introduced according to known procedures. The 4-hydroxy and 6-hydroxy groups are then protected by techniques well known to those familiar with carbohydrate chemistry. These N-alkyl-4,6-O-protected derivatives can be represented by the formula:

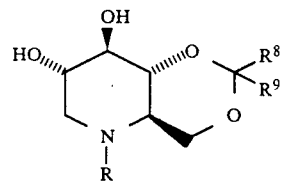

wherein $R^8$ and $R^9$ independently represent radicals as defined above. For example, utilizing 2,2-dimethoxypropane or, preferably, benzaldehyde, the corresponding 4,6-O-isopropylidene- ($R^8=R^9=CH_3$) or - 4,6-O-benzylidene ($R^8$=phenyl, $R^9$=H) N-substituted DNJ can be produced. These reactions are generally conducted in an inert organic solvent and in the presence of a strong acid which acts as catalyst. The reactions can be conducted at temperatures of from about 0° C. to about 50° C., preferably from about 10° C. to 40° C., such as from about 20° C. to about 30° C. Exemplary acid catalysts include zinc chloride, p-toluenesulfonic acid and the like. During the reaction water is removed, preferably utilizing a molecular sieve such as a 3 angstrom (Å) molecular seive.

Alternatively, starting with DNJ, the amino group can be protected and then the 4-hydroxy and 6-hydroxy groups are protected according to the above procedure. Protection of the amino group can be accomplished by methods well known to those familiar with amino acid chemistry. For example, the amino group can be protected utilizing a carbonyl compound represented by the formula

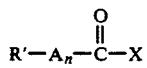

wherein R' represents alkyl radicals having from 1 to about 10 carbon atoms, and aryl, aralkyl and alkaryl radicals having from about 6 to about 26 carbon atoms; or aryl or alkylaryl or araalkyl with suitable carbon numbers, A represents oxygen; n is 0 or 1; and X represents Cl, Br, I, or $C(O)A_nR'$ wherein R', A and n have the same meanings as defined above. Exemplary amino protecting groups include carbobenzoxy, butyryl, benzoyl, and the like. These reactions are generally conducted in a polar solvent and in the presence of a base at a temperature of from about 0° C. to about 50° C., preferably from about 0° C. to about 25° C. such as from about 10° C. to 20° C. Exemplary bases include $NaHCO_3$, $NaOH$ and certain tertiary amines. Exemplary solvents include water and N,N-dimethylformamide.

It is preferred, however, that the compounds of the present invention be prepared starting with DNJ, protecting the amino group with the carbobenzoxy group and then protecting the 4-hydroxy and 6-hydroxy groups utilizing the benzylidene protecting group. Optionally, the amino protecting group can then be removed by procedures well known in the art, such as with a base, e.g., KOH, NaOH, and LiOH. In this case, an alkyl acid chloride is then reacted with the 4,6-O-benzylidene-1-deoxynojirimycin to produce the N-carboalkyl-4,6-O-benzylidene-1-deoxynojirimycin, the N-carboalkyl being reduced to the desired alkyl group in a subsequent step as discussed below. Alternately, the amino protecting group can be removed in a later step as discussed below.

In order to facilitate discussion of the remaining method steps, the N-alkyl, N-carboaryloxy, N-carboallyloxy, and N-carboalkyl DNJ derivatives will be collectively referred to as N-protected. Also, the 4,6-O-protected compounds will be referred to as 4,6-O-benzylidene compounds.

The above-described N-protected-4,6-O-benzylidene-1-deoxynojirimycin is then reacted with a dialkyltin oxide ($R^{11}R^{12}SnO$), preferably di-n-butyltin oxide, in a suitable solvent such as methanol, benzene or toluene to form the novel corresponding cyclic stannylene derivative represented by the formula:

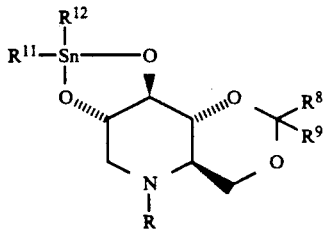

wherein R, $R^8$ and $R^9$ have the same meaning as set forth above and $R^{11}$ and $R^{12}$ independently represent alkyl radicals having from 1 to about 10 carbon atoms, such as from about 1 to about 6 carbon atoms, preferably about 4 carbon atoms.

The cyclic stannylene derivative is then reacted with an electrophilic sulfonyl compound. Suitable electrophiles are sulfonyl halides and anhydrides. Preferred electrophiles are those represented by the formula:

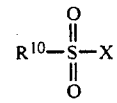

wherein X represents Cl, Br, I, and

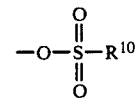

and $R^{10}$ represents optionally substituted alkyl radicals having from 1 to about 6 carbon atoms and optionally substituted aralkyl and aryl radicals. Exemplary $R^{10}$ radicals include phenyl, p-methylphenyl, trifluoromethyl ($CF_3$) and methyl. A preferred electrophile is the p-toluenesulfonyl chloride. The reactions are conducted in an inert solvent in the presence of a base and at a temperature of between about 0° C. and 100° C., preferably at a temperature of from about 0° C to about 25° C. Exemplary bases include tertiary amines such as triethylamine, and diisopropylethyl amine, pyridine, N,N-dimethylaminopyridine, 1,8-diazabicyclo[5.4.0]undec-7-ene (DBU) and 1,5-diazabicyclo[4.3.0]non-5-ene (DBN).

The resulting novel product of the reaction between the cyclic stannylene and the electrophile is predominantly the N-protected-2-O-substituted-4,6-O-benzylidene-1-deoxynojirimycin represented by the formula:

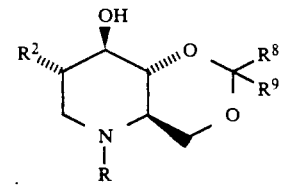

wherein $R^2$ represents a sulfonyl ester and R, $R^8$ and $R^9$ are as defined above. By predominant it is meant that the 2-O-substituted product is produced in excess of the 3-O-substituted product.

The sulfonyl ester at C-2 of the N-protected-2-O-substituted-4,6-O-benzylidene-1-deoxynojirimycin is then displaced under conditions which produce the corresponding N-protected-2,3-anhydro-4,6-O-benzylidene-1-deoxymannojirimycin represented by the formula:

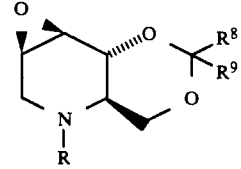

wherein R, $R^8$ and $R^9$ are as defined above. For example, utilizing a strong base such as sodium hydride, potassium hydride, a potassium or sodium alkoxide, e.g., sodium methoxide, sodium ethoxide, potassium t-butoxide and the like, or DBU, the sulfonyl ester at the 2-position is displaced, along with the oxygen, with inversion of configuration at C-2 to produce the corresponding 2,3-anhydro-1-deoxymannojirimycin. A preferred base is sodium hydride. The reaction is generally conducted in a suitable solvent in the presence of the base and at a temperature of between about 0° C. and about 120° C., preferably at a temperature of between about 0° C. and 25° C. Exemplary suitable solvents include tetrahydrofuran, methylene chloride, methanol and ethanol. A preferred solvent is tetrahydrofuran.

The N-protected-2,3-anhydro-4,6-O-benzylidene-1-deoxymannojirimycin is then reacted with a fluorine source with inversion of configuration at C-2 to produce the corresponding N-protected-4,6-O-benzylidene-1,2-dideoxy-2-fluoronojirimycin represented by the formula:

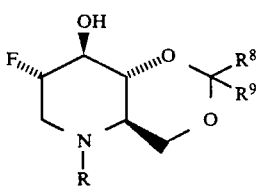

wherein R, $R^8$ and $R^9$ are as defined above. The reaction is preferably conducted neat, i.e., no solvent, at a temperature of between about 50° C. and 150° C., preferably between about 100° C. and about 140° C. Exemplary fluorine sources include those represented by the formula:

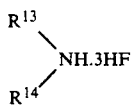

wherein $R^{13}$ and $R^{14}$ independently represent optionally substituted alkyl groups having from 1 to about 6 carbon atoms. A preferred alkyl group is isopropyl. Other fluoride sources include potassium hydrogen fluoride, hydrogen fluoride, hydrogen tetra-fluoroborate and tetra-alkylammonium fluorides (e.g. tetra-N-butylammonium fluoride).

The next step involves removal of the 4,6-O-protecting group, e.g., the benzylidene group, by methods well known to those skilled in the art. Generally, such protecting groups can be removed utilizing an acid in an appropriate solvent at room temperatures. For example, $CF_3CO_2H$ in water, $CH_3CO_2H$ in water or HCl in water can be utilized to effectively deprotect the 4- and 6-hydroxy groups. Alternatively, such protecting groups can be removed catalytically. For example, reaction with palladium on carbon at 50° C. and 50 psi $H_2$.

It should be noted that where the amino protecting group can be removed through hydrogenolysis (for example, a carbobenzoxy group), hydrogenation in the presence of palladium on carbon will remove both the nitrogen protecting group and the 4,6-O-benzylidene protecting group. Thus, deprotection can occur in one step.

Alternatively, the acyl group can be reduced utilizing borane:dimethylsulfide, lithium aluminum hydride or diborane in a suitable solvent, e.g., THF, at a temperature of from about 0° C. to about 120° C., preferably from about 0° C. to about 25° C. A preferred reducing agent is borane:dimethylsulfide Following reduction of the acyl group to the corresponding alkyl group, the 4- and 6-hydroxy protecting groups can be removed as described above.

Where other amino protecting groups are utilized, however, one can remove such groups either prior to or following deprotection of the 4-and 6-hydroxy groups utilizing well known methods and, if desired, replace such groups with an appropriate alkyl group by methods well known in the art.

The subject 1,2-dideoxy-2-fluoronojirimycin and N-derivatives thereof manifest glycosidase inhibition activity. It is contemplated that certain intermediates disclosed herein will manifest similar activity. Thus, pharmaceutical compositions comprising one or more of the fluoro analogs and/or intermediates can be administered to a patient for this purpose. Such compositions, which may contain acceptable diluents and/or carriers, can be prepared by reference to general texts in the field such as, for example, *Remington's Pharmaceutical Sciences*, Ed. Arthur Osol, 16th ed., 1980, Mack Publishing Co.

Contemplated equivalents of the general formulas set forth above for the DNJ analogs and derivatives as well as the intermediates are compounds otherwise corresponding thereto and having the same general properties wherein one or more of the various R groups are simple variations of the substituents as defined therein, e.g., wherein R is a higher alkyl group. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. Methanol, toluene, benzaldehyde and triethylamine were dried over 3 Å molecular sieves. Methylene chloride and tetrahydrofuran were purchased as anhydrous grade from Aldrich Chemical Co. and used as received. All proton and carbon NMR spectra were obtained on either a Varian VXR-300 or VXR-400 nuclear magnetic resonance spectrometer.

EXAMPLE 1

Preparation of N-Carbobenzoxy-4,6-O-benzylidene-1-deoxynojirimycin.

A total of 75.0 g (0.46 moles) of 1-deoxynojirimycin was dissolved in 1500 mL of saturated aqueous sodium bicarbonate and then treated with 73.5 mL (87.8 g, 0.52 moles) of 95% benzyl chloroformate at room temperature using an overhead stirrer under a nitrogen atmosphere for eighteen hours. The solution was extracted once with 250 mL of methylene chloride to remove any benzyl chloride and unreacted benzyl chloroformate. The aqueous solution was then extracted ten times with 500 mL of ethyl acetate. After drying over anhydrous magnesium sulfate, filtering and removal of solvent, 102.8 g (76% yield) of a colorless oil was obtained which was identified as N-carbobenzoxy-1-deoxynojirimycin of sufficient purity for use in the next step; 300 MHz $^1$H NMR ($\delta$, CD$_3$OD) 7.40–7.20 (m, 5H), 5.15 (s, 2H), 4.23 (br m, 1H), 4.05 (br d, J=8.0 Hz, 1H), 3.87 (dd, J=4.0 and 6.0 Hz, 1H), 3.85–3.78 (m, 2H), 3.78–3.70 (m, 2H), and 3.45 (br d, J=8.0 Hz, 1H).

To 102 g (0.345 mol) of N-carbobenzoxy-1-deoxynojirimycin, which had been dried in vacuo over phosphorous pentoxide overnight, was added 1000 mL of benzaldehyde (dried with 3 Å molecular sieves). This was warmed at 40° C. while swirling on a rotory evaporator (no vacuum) until the oil was fully dissolved, then split in half and each half transferred to a 5 L three-necked flask and an additional 200 mL of benzaldehyde used to rinse the flask and 100 mL added to each reaction. After placing each reaction flask under nitrogen, 101 g of freshly activated 3 Å molecular sieves were added and then 257.6 g of anhydrous zinc chloride (dried in vacuo overnight over P$_2$O$_5$) was added and some warming observed. After stirring for five hours at room temperature, 1000 mL of ethyl acetate was added, each flask cooled in an ice bath and then 1500 mL of a cold saturated aqueous solution of sodium bicarbonate was added. Some foaming was observed. The white precipitate which formed was filtered and washed with ethyl acetate. The filtrate was separated and the organic layer washed with saturated sodium chloride, dried with magnesium sulfate and filtered. The organic layer from each reaction were combined and stripped at 40° C. to afford a benzaldehyde solution of the desired product. This was then poured into 10 L of hexane with stirring, the precipitate collected and washed with hexane and air dried. This material was dissolved in approximately 1200 mL of hot ethyl acetate, hexane added to the cloud point (approx. 1500 mL), where-upon crystallization occurred. After cooling to room temperature, the preoipitate was collected and washed well with hexane to afford 91.1 g (68%) of N-carbobenzoxy-4,6-O-benzylidene-1-deoxynojirimycin as a white solid, mp 147°–148° C.; 300 MHz $^1$H NMR ($\delta$, CD$_3$OD) 7.53–7.28 (m, 10H), 5.61 (s, 1H), 5.14 (s, 2H), 4.77 (dd, $J_{5,6}$=4.6 Hz, $J_{6,6}$=11.0 Hz, 1H, H$_6$), 4.38 (t, $J_{5,6'}$=$J_{6,6'}$=11.0 Hz, 1H, H$_{6'}$), 4.16 (dd, $J_{1,2}$=4.2 Hz, $J_{1,1'}$=13.4 Hz, 1H, H$_1$), 3.69–3.50 (complex m, 3H, H$_2$, H$_3$ and H$_4$), 3.35 (ddd, $J_{4,5}$=$J_{5,6}$=11.0 Hz, $J_{5,6}$=4.6 Hz, 1H, H$_5$) and 2.97 (dd, $J_{1',2}$=9.3 Hz, $J_{1,1'}$=13.4 Hz, 1H, H$_{1'}$); 75 MHz $^{13}$C NMR (CD$_3$OD) 156.7, 139.4, 138.0, 129.9, 129.7, 129.3, 129.2, 129.1, 127.6, 102.8, 81.9, 77.5, 71.5, 70.6, 68.6, 55.9 and 50.5 ppm; mass spectrum (m/e) 386 (M+H), 361, 327 and 280; and Anal. Calcd. for C$_{21}$H$_{23}$NO$_6$: C (65.45), H (6.01) and N (3.63); Found C (65.41), H (6.19) and N (3.59).

EXAMPLE 2

Preparation of N-Butyryl-4,6-O-benzylidene-1-deoxynojirimycin

To a solution of 44.5 g (0.79 moles) of potassium hydroxide in 425 mL of methanol and 155 mL of water, was added 45 g (0.12 moles) of N-carbobenzoxy-4,6-O-benzylidene-1-deoxynojirimycin and the mixture refluxed under a nitrogen atmosphere for sixty-seven hours. After cooling to room temperature, the methanol was removed under reduced pressure, the residue transferred to a 2 L 3-necked flask and 100 mL of tetrahydrofuran added. The suspension was vigorously stirred, cooled in ice and 15.5 mL (15.9 g, 0.15 mol, 1.24 equiv.) of butyryl chloride added over ten minutes. After removal of the ice bath, the reaction was stirred at room temperature and monitored by tlc on silica gel using (20% v:v) methanol/methylene chloride as eluent. After 3 hours, an additional 3 mL of butyryl chloride was added and this was repeated 3xs until tlc indicated complete disappearance of the amine. The reaction was cooled in ice and acidified to neutral pH with 1N hydrochloric acid. The tetrahydrofuran was removed under reduced pressure and the aqueous layer extracted twice with 700 mL of methylene chloride. After combining, the organic layers were washed with saturated aqueous sodium bicarbonate, dried over anhydrous magnesium sulfate, filtered and concentrated to afford 49.3 g of a clear oil. This was chromatographed on a Waters Prep 500A chromatogram using two silica gel cartridges and eluting first with 50:50 (v:v) ethyl acetate/hexane and then ethyl acetate. In this manner one obtains 33.1 g (88% yield) of a clear colorless oil which was identified as N-butyryl-4,6-O-benzylidene-1-deoxynojirimycin. A sample was prepared for elemental analysis by re-chromatography on a chromatatron using silica gel and eluting with ethyl acetate, stripping and drying under vacuum over phosphorous pentoxide; 300 MHz $^1$H NMR ($\delta$, CDCl$_3$) 7.55–7.33 (m, 5H), 5.54 (s, 1H), 4.87 (dd, $J_{5,6}$=4.5 Hz, $J_{6,6'}$=11.3 Hz, 1H, H$_6$), 4.61 (t, $J_{5,6'}$=$J_{6,6'}$=11.3 Hz, 1H, H$_{6'}$), 3.95 (br s, 1H, OH), 3.79 (d, J=3.3 Hz, 1H, OH), 3.72 (dd, $J_{1,2}$=4.2 Hz, $J_{1,1'}$=13.8 Hz, 1H, H$_1$), 3.70–3.41 (complex m, 3H, H$_2$, H$_3$ and H$_4$), 3.21 (br ddd, $J_{5,6}$=4.5 Hz, $J_{4,5}$=$J_{5,6'}$=11.3 Hz, 1H, H$_5$), 2.78 (dd, $J_{1',2}$=9.3 Hz, $J_{1,1'}$=13.8 Hz, 1H, H$_{1'}$), 2.32–2.13 (m, 2H), 1.61 (sextuplet, J=7.4 Hz, 2H) and 0.97 (t, J=7.4 Hz, 3H); 75 MHz $^{13}$C NMR (CDCl$_3$) 173.5, 137.4, 129.3, 128.3, 126.4, 101.6, 79.5, 77.1, 70.1, 69.5, 56.4, 49.9, 36.7, 18.4 and 13.9 ppm; mass spectrum (m/e) 328 (M+Li); and Anal. Calcd. for C$_{17}$H$_{23}$NO$_5$: C(63.53), H(7.23) and N(4.36); Found C(63.29), H(7.33) and N(4.31).

EXAMPLE 3

Preparation of N-Carbobenzoxy-4,6-O-benzylidene-2,3-O-(di-n-butylstannylene)-1-deoxynojirimycin.

To a mixture of 0.50 g (1.30 mmol) of N-carbobenzoxy-4,6-O-benzylidene-1-deoxynojirimycin and 0.34 g (1.36 mmol) of di-n-butyltin oxide (both dried in vacuo over P$_2$O$_5$ overnight), under a nitrogen atmosphre, was added 5 mL of dry methanol (dried over 3 Å molecular sieves) and the mixture refluxed for two hours. After cooling to room temperature, the volatiles were removed under vacuum, toluene added and then removed twice to afford N-carbobenzoxy-2,3-O-(di-n-butylstannylene)-4,6-O-benzylidene-1deoxynojirimycin as a white solid; 300 MH$_2$ $^1$H NMR ($\delta$, CDCl$_3$) 7.50–7.25 (m, 10H), 5.42 (s, 1H), 5.05 (AB quartet, J$_{AB}$=12.3 Hz, u$_{AB}$=14.2 Hz, 2H), 4.80 (dd, J$_{6,6'}$=11.8 Hz, J$_{5,6}$=4.5 Hz, 1H H$_6$), 4.56 (dd, J$_{6,6'}$=11.8 Hz, J$_{5,6'}$=11.4 Hz, 1H, H$_{6'}$), 4.39 (dd, J$_{1,1'}$=12.7 Hz, J$_{1,2}$=4.1 Hz, H$_1$), 3.51 (dd, J$_{3,4}$=9.0 Hz, J$_{4,5}$=9.0 Hz, 1H, H$_4$), 3.29 (ddd, J$_{5,6}$=4.4 Hz, J$_{4,5}$=J$_{5,6'}$=10.5 Hz, 1H, H$_5$), 3.17–3.03 (m, 2H, H$_2$ and H$_3$), 2.62 (dd, J$_{1,1'}$=12.7 Hz, J$_{1',2}$=10.2 Hz, 1H, H$_{1'}$) and 1.60–0.76 (m, 18H); and mass.spectrum (m/e) 624 (M+Li).

EXAMPLE 4

Preparation of N-Carbobenzoxy-2-O-(p-toluenesulfonyl)-4,6-O-benzylidene-1-deoxynojirimycin.

A mixture of 25.8 g (66.9 mmol) of N-carbobenzoxy-4,6-O-benzylidene-1-deoxynojirimycin and 17.5 g (70.2 mmol, 1.05 equiv.) of di-n-butyltin oxide, both previously dried in vacuo over phosphorous pentoxide, and 260 mL of anhydrous methanol were refluxed under a nitrogen atmosphere for two hours. The methanol was removed, toluene was added and removed in vacuo. The residue was dissolved in 250 mL of anhydrous methylene chloride under nitrogen, 7.71 g (76.3 mmol, 1.14 equiv.) of triethylamine added and then a solution of 13.39 g (70.2 mmol, 1.05 equiv.) of recrystallized p-toluenesulfonyl chloride in 50 mL of anhydrous methylene chloride was added dropwise over ten minutes. After stirring for twenty hours, 260 mL of saturated aqueous sodium bicarbonate solution was added and the tin salts filtered (with difficulty). The organic layer was separated, washed with saturated sodium chloride, dried with anhydrous magnesium sulfate, filtered and concentrated to afford 38.7 g of a foam. This was chromatographed on a Waters Prep 500A Chromatogram using two silica gel cartridges and 50:50 (v:v) ethyl acetate/hexane as eluant to afford 34.0 g (94%) of a white foam, which was identified as N-carbobenzoxy-2-0-(p-toluenesulfonyl)-1-deoxynojirimycin. An analytical sample was prepared by recrystallization from ethyl acetate/hexane, mp 7 115–117° C.; 300 MHz $^1$H NMR ($\delta$, CDCl$_3$) 7.82 (d, J=7.8 Hz, 2H), 7.50–7.35 (m, 10H), 7.31 (d, J=7.8 Hz, 2H), 5.51 (s, 1H), 5.12 (s, 2H), 4.76 (dd, J$_{5,6}$=4.5 Hz, J$_{6,6'}$=11.4, 1H, H$_6$), 4.38 (ddd, J$_{1',2}$=9.3 Hz, J$_{1,2}$=4.8 Hz, J$_{2,3}$=7.6 Hz, 1H, H$_2$), 4.32 (t, J$_{6,6'}$11.4 Hz, J$_{5,6'}$=9.5 Hz, 1H, H$_{6'}$), 4.31 (dd, J$_{1,2}$=4.8 Hz, J$_{1,1'}$=13.6 Hz, 1H, H$_1$), 3.78 (dt, J$_{2,3}$=J$_{3,4}$=9.4 Hz, J$_{3,OH}$=2.6 Hz, 1H, H$_3$), 3.59 (t, J$_{3,4}$=J$_{4,5}$=9.4 Hz, 1H, H$_4$), 3.26 (ddd, J$_{4,5}$=9.4 Hz, J$_{5,6}$=4.5 Hz, J$_{5,6'}$=11.4 Hz, 1H, H$_5$), 3.04 (dd, J$_{1',2}$=9.3 Hz, J$_{1,1'}$=13.6 Hz, 1H, H$_{1'}$), 2.63 (d, J$_{3,OH}$=2.6 Hz, 1H, OH) and 2.41 (s, 3H); 75 MHz $^{13}$C NMR (CDCl$_3$) 154.8, 145.2, 137.0, 135.8, 133.2, 129.8, 129.3, 128.7, 128.4, 128.3, 128.1, 126.2, 101.8, 79.9, 78.1, 73.9, 69.2, 67.8, 54.2, 47.1 and 21.7 ppm; mass spectrum (m/e) 546 (M+Li) and 374; and Anal. Calcd. for C$_{28}$H$_{29}$NO$_8$S: C (62.32), H (5.42) and N (2.66); Found C (62.65), H (5.40) and N (2.62).

EXAMPLE 5

Preparation of N-Carbobenzoxy-2,3-anhydro-1-deoxy mannojirimycin, Method A.

To 7.40 g of an 80% sodium hydride in oil dispersion (5.90 g, 247 mmol) under a nitrogen atmosphere, was added 280 mL of anhydrous tetrahydrofuran. After brief stirring, the solids were allowed to settle and the solution withdrawn via syringe. To this was then added a solution of 32.4 g (60 mmol) of N-carbobenzoxy-2–0-(p-toluenesulfonyl)-4,6-O-benzylidene-1-deoxynojirimycin in 350 mL of anhydrous tetrahydrofuran. After stirring at room temperature for eight and one-half hours, the slurry was slowly poured into a solution of 25 mL of acetic acid in 1400 mL of water under a nitrogen atmosphere. The resulting mixture was extracted with ethyl acetate, separated and the organic layer washed with saturated aqueous sodium bicarbonate, saturated aqueous sodium chloride, dried with magnesium sulfate, filtered and concentrated to afford 24.0 g of a slightly yellow-colored solid. This was dissolved in methylene chloride and hexane added to induce crystallization. The resulting white crystals were collected, washed with hexane and air-dried to afford 20.0 g (91% yield) of N-carbobenzoxy-2,3-anhydro-4,6-O-benzylidene-1-deoxymannojirimycin, mp 104–105° C.; 300 MH$_2$ 1H NMR ($\delta$, CDCl$_3$) 7.67–7.53 (complex m, 10H), 5.67 (s, 1H), 5.16 (s, 2H), 4.76 (br s, 1H, H$_{6'}$), 4.59 (d, J$_{1,1'}$=15.0 Hz, 1H, H$_1$), 4.02 (dd, J$_{5,6}$=4.0 Hz, J$_{6,6'}$=11.4 Hz, 1H, H$_6$), 4.08 ($\delta$, J$_{4,5}$=10.0 Hz, 1H, H$_4$), 3.46 (dd, J$_{1',2}$=0.9 Hz, J$_{1,1'}$=15.0 Hz, 1H H$_{1'}$), 3.40 (d, J$_{2,3}$=3.0 Hz, 1H, H$_2$ or H$_3$), 3.25 (d, J$_{2,3}$=3.0 Hz, 1H, H$_2$ or H$_3$) and 3.10 (ddd, J$_{5,6}$=4.0 Hz, J$_{5,6}$=J$_{3,4}$=10.0 Hz, 1H, H$_5$); 75 MHz $^{13}$C (CDCl$_3$) 156.2, 137.8, 136.6, 129.7, 129.1, 128.9, 128.8, 128.5, 126.6, 102.8, 73.0, 70.4, 68.0, 56.0, 54.7, 50.4 and 46.6 ppm; mass spectrum (m/e) 374 (M+Li); and Anal. Calcd. for C$_{21}$H$_{21}$NO$_5$: C (68.64), H (5.77) and N (3.81); Found C (68.42), H (5.89) and N (3.77).

EXAMPLE 6

Preparation of N-carbobenzoxy-2,3-anhydro-4,6-O-benzylidene-1-deoxymannojirimycin, Method B.

To a mixture of 0.385 g (0.10 mmol) of N-carbobenzoxy-4,6-O-benzylidene-1-deoxynojirimycin and 0.267 g (0.105 mmol) of dibutyltin oxide, under nitrogen atmosphere, was added 5 mL of dry methanol and the mixture refluxed for two hours. After cooling, the methanol was removed in vacuo and further dried with two toluene azeotropes. The crude stannylene was dissolved in 10 mL of dry methylene chloride and placed under nitrogen atmosphere and cooled to −78° C. To this was added 100 µL dry pyridine and 178 µL of trifluoromethanesulfonic anhydride, and the reaction allowed to warm to room temperature over 16 hours. The mixture was diluted with 25 mL of methylene chloride and extracted 2×20 mL with saturated sodium bicarbonate. The organic phase was dried over MgSO$_4$, filtered, and conc. in vacuo to yield after silica gel chromatography using 1% CH$_3$OH, 99% CH$_2$Cl$_2$, 130 mg (36% yield) of a white solid which was identified as N-carbobenzoxy-2,3-anhydro-4,6-O-benzylidene-1-deoxynojirimycin, mp 104–105° C.

EXAMPLE 7

Preparation of N-Carbobenzoxy-4,6-O-benzylidene-1,2-dideoxy-2-fluoronojirimycin.

In a 250 mL round-bottom flask was placed 14.6- g (39.9 mmol) of N-carbobenzoxy-2,3-anhydro-1-deoxymannojirimycin and 29.34 g(196 mmol, 4.9 equiv.) of diisopropylamine trihydrofluoride. The flask was then placed on a rotary evaporator under a nitrogen atmosphere and with swirling immersed in an oil bath maintained at 125° C. After swirling for seventy hours, the flask was cooled and the mixture dissolved in ethyl acetate and saturated aqueous sodium bicarbonate solution. After separating, the organic layer was washed with 0.2N hydrochloric acid, saturated aqueous sodium chloride, dried over anhydrous magnesiun sulfate, filtered and stripped to afford 14.2 g of a brown oil, whose $^1$H and $^{13}$C NMR spectra were consistent with the presence of two isomeric fluorohydrins in a 2.8:1 ratio. The crude material was chromatographed on a Waters Prep 500A chromatogram using two silica gel cartridges and first 100% methylene chloride and then 2% (v:v) methanol/methylene chloride as eluant. The first isomer to elute (5.67 g, 37%) corresponded to the major isomer. It was recrystallized from chloroform/hexane to afford 4.30 g (28%) of a white solid which was identified as N-carbobenzoxy-4,6-O-benzylidene-1,2-dideoxy-2-fluoronojirimycin, mp 94°-95° C.; 300 MHz $^1$H NMR (δ, CDCl$_3$) 7.57–7.34 (m, 10H), 5.57 (s, 1H), 5.17 (AB quartet, $J_{A,B}=12.1$ Hz, $u_{A,B}15.0$ Hz, 2H, CBZ), 4.87 (dd, $J_{5,6}=4.6$ Hz, $J_{6,6'}=11.3$ Hz, 1H, H$_6$), 4.53 (dddd, $J_{1,2}=4.6$ Hz, $J_{1',2}8.7$ Hz, $J_{2,3}=6.6$ Hz, $J_{2,F}=48.4$ Hz, 1H, H$_2$), 4.26 (t, $J_{5,6'}=J_{6,6}=11.3$ Hz, 1H, H$_{6'}$), 4.25 (ddd, $J_{1,2}=4.6$ Hz, $J_{1,1'}=14.1$ Hz, $J_{1,F}13.3$ Hz, 1H, H$_1$), 3.88 (ddd, $J_{2,3}=6.6$ Hz, $J_{3,4}=9.6$ Hz, $J_{3,F}=18.3$ Hz, 1H, H$_3$), 3.65 (t, $J_{3,4}=J_{4,5}=9.6$ Hz, 1H, H$_4$), 3.36 (ddd, $J_{5,6}=4.6$ Hz, $J_{5,6}=10.2$ Hz, $J_{4,5}=9.6$ Hz, 1H, H$_5$), 3.26 (ddd, $J_{1,2}=8.7$ Hz, $J_{1,1'}=14.1$ Hz, $J_{1',F}=6.0$ Hz, 1H, H$_{1'}$) and 3.06 (br s, 1H, OH); 75 MHz $^{13}$C NMR (CDCl$_3$) 154.9, 137.0, 135.7, 129.3, 128.6, 128.4, 128.3, 128.1, 126.2, 101.7, 89.5 (d, $J_{C2,F}=180.5$ Hz, C$_2$), 79.6 (d, $J_{C4,F}=8.6$ Hz, C$_4$), 74.4 (d, $J_{C3,F}=22.0$ Hz, C$_3$), 69.3, 67.8, 53.4 and 46.1 (d, $J_{C1,F}=27.4$ Hz, C$_1$) ppm; mass spectrum (m/e) 388 (M+H), 282 and 238; and Anal. Calcd. for C$_{21}$H$_{22}$FNO$_5$: C (65.10), H (5.74) and N (3.61); Found C (65.37), H (5.82) and N (3.69).

EXAMPLE 8

Preparation of 1,2-Dideoxy-2-fluoronojirimycin

In a Fisher-Porter bottle was placed 3.90 g (10.1 mmol) of N-carbobenzoxy-4,6-O-benzylidene-1,2-dideoxy-2-fluoronojirimycin, 38mL of methanol and 10 mL of water. To the homogeneous solution under a nitrogen atmosphere was added 3.9 g of a 10% palladium on carbon catalyst. The reactor was sealed, flushed 3 times with 40 psi of nitrogen and 4 times with 50 psi of hydrogen. The reactor was charged with 50 psi of hydrogen and heated at 50° C. for twenty-one hours. After cooling, the reactor was flushed with nitrogen, opened and the contents filtered through celite, which was then washed with water. The filtrate was extracted once with ethyl acetate to remove organics and the aqueous layer was concentrated under vacuum at 50° C. to afford an oil. The remaining water was removed by azeotrope with ethanol to provide 1.2 g of a white solid, whose $^1$H NMR was consistent with 1,2-dideoxy-2-fluoronojirimycin. This was dissolved in water, filtered to remove a slight grey color and stripped again. This was recrystallized by dissolving in a minimal amount of water, followed by ethanol and then hexane to afford 0.58 g (35%) of a white solid, which was identified as 1,2-dideoxy-2-fluoronojirimycin, mp 161.5°–162.5° C.; 400 MHz $^1$H NMR (δ, D$_2$O) 4.38 (dddd, $J_{1'',2}=5.5$ Hz, $J_{1,2}=10.8$ Hz, $J_{2,3}=9.5$ Hz, $J_{2,F}50.5$ Hz, 1H, H$_2$), 3.83 (dd, $J_{5,6}=3.0$ Hz, $J_{6,6'}=11.7$ Hz, 1H, H$_6$), 3.64 (dd, $J_{5,6'}=6.0$ Hz, $J_{6,6'}=11.7$ Hz, 1H, H$_{6'}$), 3.62 (dt, $J_{2,3}=J_{3,4}=9.5$ Hz, $J_{3,F}=14.5$ Hz, 1H, H$_3$), 3.39 (ddd, $J_{1,2}=5.5$ Hz, $J_{1,1'}=12.3$ Hz, $J_{1,F}=1.5$ Hz, 1H, H$_1$), 3.28 (t, $J_{3,4}=J_{4,5}=9.5$ Hz, 1H, H$_4$), 2.65 (ddd, $J_{1,1'}=12.3$ Hz, $J_{1',2}=10.7$ Hz, $J_{1',F}=4.9$ Hz, 1H, H$_{1'}$) and 2.56 (ddd, $J_{5,6}=3.0$ Hz, $J_{5,6'}=6.0$ Hz, $J_{4,5}=9.5$ Hz, 1H, H$_5$); 75 MHz $^{13}$C NMR (D$_2$O) 94.6 (d, $J_{C2,F}=176.7$ Hz, C$_2$), 79.9 (d, $J_{C3'F}=16.7$ Hz, C$_3$), 74.3 (d $J_{C4,F}=8.6$ Hz, C$_4$), 64.3, 63.5 and 49.3 (d, $J_{C1'F}=24.0$ Hz, C$_1$) ppm; mass spectrum (m/e) 166 (M+H), 148 and 134; and Anal. Calcd. for C$_6$H$_{12}$FNO$_3$: C (43.63), H (7.34) and N (8.48); Found C (43.79), H (7.40) and N (8.37).

EXAMPLE 9

Preparation of N-Butyryl-2-0-(p-toluenesulfonyl)-4,6-O-benzylidene-1-deoxynojirimycin In a IL round-bottom flask was placed 27.11 g (84 mmol) of N-butyryl-4,6-O-benzylidene-1-deoxynojirimycin (previously dried under vacuum over phosphorous pentoxide), 370 mL of dry toluene and then 22.05 g (88 mmol, 1.05 equiv.) of dibutyltin oxide. The mixture was refluxed under a nitrogen atmosphre with azeotrope removal of water for two hours. The solution was cooled to room temperature, 9.63 g (95 mmol, 1.13 equiv.) of dry triethylamine added and then a solution of 17.69 g (93 mmol, 1.1 equiv.) of recrystallized p-toluenesulfonyl chloride in 45 mL of toluene over ten minutes. After stirring at room temperature for twenty-two hours, the toluene layer was washed with 1 N hydrochloric acid, dried over anhydrous magnesium sulfate, filtered and stripped. The residue was chromatographed on a Waters Prep 500A chromatogram using two silica gel cartriges and eluting first with a 20% (v:v) ethyl acetate/hexane and then 50% ethyl acetate/hexane to elute the desired product (28.0 g, 70% yield) and then 100% ethyl acetate to recover starting material (4.4 g, 84% conversion). The desired product was identified as N-butyryl-2-O-(p-toluenesulfonyl)-4,6-O-benzylidene-1-deoxynojirimycin; 300 mHz $^1$H NMR (δ, CDCL$_3$) 7.87 (d, J=8.3 Hz, 2H), 7.52–7.35 (m,7H), 5.54 (s, 1H), 4.88 (dd, $J_{5,6}=4.5$ Hz, $J_{5,6'}=11.5$ Hz, 1H$_6$), 4.49 (t, $J_{5,6'}=J_{6,6'}=11.5$ Hz, 1H, H$_{6'}$), 4.35 (ddd, $J_{1,2}=4.4$ Hz, $J_{1',2}=9.0$ Hz, $J_{2,3}=9.5$ Hz, 1H, H$_2$), 4.04 (dd, $J_{1,2}=4.4$ Hz, $J_{1,1'}=14.3$ Hz, 1H, H$_1$), 3.78 (dt, $J_{3,OH}=2.6$ Hz, $J_{2,3}=J_{3,4}=9.5$ Hz, 1H, H$_3$), 3.64 (t, $J_{3,4}=J_{4,5}=9.5$ Hz, 1H, H$_4$), 3.33 (ddd, $J_{4,5}=9.5$ Hz, $J_{5,6}=4.5$ Hz, $J_{5,6'}=11.5$ Hz, 1H, H$_5$), 3.22 (dd, $J_{1',2}=9.0$ Hz, $J_{1,1'}=14.3$ Hz, 1H, H$_{1'}$), 2.85 (br d, $J_{3,OH}=2.6$ Hz, 1H, OH), 2.36–2.18 (m, 2H), 1.64 (sextuplet, J=7.5 Hz, 2H) and 0.99 (t, J=7.5 Hz, 3H); 75 MHx $^{13}$C NMR (CDCl$_3$) 173.4, 145.3, 137.1, 132.9, 129.8, 129.2, 128.2, 128.0, 126.1, 101.6, 79.3, 78.5, 73.6, 69.1, 55.4, 47.9, 36.3, 21.6, 18.3 and 13.7 ppm; and mass spectrum (m/e) 482 (M+Li), 476 (M+H) and 310.

EXAMPLB 10

Preparation of N-Butyryl-2,3-anhydro-4,6-O-benzylidene-1-deoxymannojirimycin.

In a IL three-necked flask equipped with an overhead strirrer was placed 7.22 of an 80% sodium in oil dispersion(5.8 g, 0.24 mol, 4.1 equiv.). After placing the flask under a nitrogen atmosphere, the sodium hydride was washed with 250 mL of anhydrous tetrahydrofuran, the solvent removed via a canula and the flask cooled in an ice bath. To this was added a solution of 28.0 g (59 mmol) of N-butyryl-2-O-(p-toluenesulfonyl)-4,6-O-benzylidene-1-deoxynojirimycin in 200 mL of anhydrous tetrahydrofuran over a ten minute period and the temperature maintained below 10° C. an additional 2×25 mL of anyhdrous tetrahydrofuran was used to rinse the flask containing tosylate and added to the reaction. The ice bath was removed and the reaction stirred at room temperature for twenty-one hours. In a 3üL flask was placed 990 mL of water and 20 mL of acetic acid. This was cooled in ice and placed under a nitrogen atmosphere. To this was then slowly added the reaction mixture while maintaining the temperature below 15° C. A white precipitate was observed. This was dissolved in 500 mL of methylene chloride, the layers separated and the organic layer washed with saturated aqueous sodium bicarbonate, dried over anhydrous magnesium sulfate, filtered and stripped to afford 17.7 g of an off-white solid. This was recrystallized from methylene chloride and hexane to afford 15.6 g (87% yield) of pure product which was identified as N-butyryl-2,3-anhydro-4,6-O-benzylidene-1-deoxynojirimycin, mp 120°-120.5° C.; 300 MHz $^1$H NMR (68 , CDCL$_3$) 7.58–7.49 (m, 2H), 7.46–7.37 (m, 3H), 5.71 (s, 1H), 5.34 (t, $J_{5,6'}=J_{6,6'}=11.0$ Hz, 1H, H$_{6'}$), 4.50 (dd, $J_{5,6}=4.0$ Hz, $J_{6,6'}=11.0$ Hz, 1H, H$_6$), 4.19 (br d, $J_{1,1'}=14.9$ Hz, 1H, H$_1$), 4.15 (d, $J_{4,5}=10.1$ Hz, 1H, H$_4$), 3.57 (d, $J_{1,1'}=$14.9 Hz, 1H, H$_{1'}$), 3.39 (d, $J_{2,3}=3.5$ Hz, 1H, H$_3$), 3.25 (br d, $J_{2,3}=3.5$ Hz, 1H, H$_2$), 3.05 (ddd, $J_{4,5}=10.1$ Hz, $J_{5,6}=4.0$ Hz, $J_{5,6'}=11.0$ Hz, 1H, H$_5$), 2.37–2.18 (m, 2H), 1.73–1.58 (m, 2H) and 0.99 (t, J=7.5 Hz, 3H); 75 MHz $^{13}$C NMR (CDCl$_3$) 174.6, 137.3, 129.1, 128.3, 126.1, 102.2, 71.2, 70.1, 57.6, 54.3, 49.7, 47.2, 36.6, 18.2 and 13.8 ppm; mass spectrum (m/e) 310 (M+Li); and Anal. Calcd. for C$_{17}$H$_{21}$NO$_4$: C (67.31), H (6.98) and N (4.62); Found C (67.15), H (7.28) and N (4.33).

EXAMPLE 11

Preparation of N-Butyryl-4,6-O-benzylidene-1,2-dideoxy-2-fluoronojirimycin

In a 250 mL round-bottom flask were placed 15.24 g (50.2 mmol) of N-butyryl-2,3-anhydro-4,6-O-benzylidene-1-deoxymannojirimycin and 30.5 g (189 mmol, 6 equiv.) of diiospropylamine trihydrofluoride. The flask was then placed on a rotovary evaporator under a nitrogen atmosphere and with swirling immersed in an oil bath maintained at 125° C. After swirling for fifty-four hours, the flask was cooled and the mixture dissolved in ethyl acetate and saturated aqueous sodium bicarbonate solution. After separating the layers, the organic layer was washed with 0.2N hydrochloric acid and saturated sodium chloride, dried over anhydrous magnesium sulfate, filtered and stripped to afford 12.2 g of crude material whose $^1$H and $^{13}$C NMR indicated a 2.8:1 mixture of isomeric fluorohydrins. These were separated on a Waters Prep 500A chromatogram using two silica gel cartridges and first methylene chloride, followed by 2% (v:v) methanol/methylene chloride as eluant. The first isomer to elute (5.7 g, 35%), which corresponded to the major isomer, was identified as N-butyryl-4,6-O-benzylidene-1,2-dideoxy-2-fluoronojirimycin. It was recrystallized from chloroform and hexane to afford 6.0 g of material which contained chloroform in the crystals. This was suitable for the subsequent chemistry. An analytical sample was prepared by recrystallizing 200 mg from ethyl acetate/hexane to afford 143 mg of pure compound, mp 111°-112° C.; 300 MHz $^1$H NMR(δ, CDCl$_3$) 7.57–7.48 (m, 2H), 7.47–7.38 (m, 3H), 5.61 (s, 1H), 4.96 (dd, $J_{5,6}=4.4$ Hz, $J_{6,6'}=11.3$ Hz, 1H, H$_6$), 4.60 (dddd, $J_{1,2}=4.1$ Hz, $J_{2,3}=5.7$ Hz, $J_{1',2}=7.5$ Hz, $J_{2,F}=48.3$ Hz, 1H, H$_2$), 4.31 (t, $J_{5,6'}=J_{6,6'}=11.3$ Hz, 1H, H$_6$), 4.03–3.87 (m, 1H, H$_3$), 3.91 (ddd, $J_{1,2}=4.1$ Hz, $J_{1,1'}=14.5$ Hz, $J_{1,F}=16.3$ Hz, 1H, H$_1$), 3.75 (t, $J_{4,5}=J_{3,4}=9.7$ Hz, 1H, H$_4$), 3.54 (ddd, $J_{4,5}=9.7$ Hz, $J_{5,6}=4.4$ Hz, $J_{5,6'}=11.3$ Hz, 1H, H$_5$), 3.45 (dd, $J_{1',2}=7.5$ Hz, $J_{1,1'}=14.6$ Hz, 1H, H$_{1'}$), 2.43–2.25 (m, 2H), 1.67 (sextuplet, J=7.4 Hz, 2H) and 1.01 (t, J=7.4 Hz, 3H); 75 MHz $^{13}$C NMR (CDCl$_3$) 173.8, 137.2, 129.5, 128.5, 126.4, 102.1, 90.6 (d, $J_{C2,F}=181.5$ Hz, C$_2$), 79.3 (d, $J_{C4,F}=9.0$ Hz, C$_4$), 74.5 (d, $J_{C3,F}=23.3$ Hz, C$_3$), 69.4, 54.3, 46.7 (d, $J_{Cl,F}=29.3$ Hz, C$_1$), 36.5 18.5 and 13.9 ppm; mass spectrum (m/e) 330 (M+Li); and Anal. Calcd. for C$_{17}$H$_{22}$FNO$_4$; C (63.13), H (6.87) and N (4.33); Found C (62.98), H (6.80) and N (4.17).

EXAMPLE 12

Preparation of N-Butyl-1,2-dideoxy-2-fluoronojirimycin

To a solution of 1.50 g (4.64 mmol) of N-butyryl-4,6-O-benzylidene 1,2-dideoxy-2-fluoronojirimycin in 8.9 mL of anhydrous tetrahydrofuran under a nitrogen atmosphere of 0° C., was added 3 mL (30 mmol, 6.5 equiv.) of 10 M borane:methyl sulfide complex over a ten-minute period. The ice bath was removed and the reaction stirred at room temperature for four hours. After cooling to 0° C., 8.4 mL of anhydrous methanol was slowly added over ten minutes and stirring continued for an additional thirty minutes. The volatiles were removed under reduced pressure, the residue dissolved in 50 mL of methylene chloride, extracted twice with a saturated aqueous sodium bicarbonate solution, dried over anhydrous magnesium sulfate, filtered and stripped to afford 1.43 g of a clear oil. This was dissolved in a mixture of 15 mL of water and 15 mL of trifluoroacetic acid and stirred at room temperature for three hours. The volatiles were removed under reduced pressure, toluene added and removed, then methanol added and removed. The residue was triturated with diethyl ether. The residue was dried under vacuum to afford 1.0 g of an off-white solid. An Amberlite CG-400 (Cl$^-$ form) resin was conditioned as follows; in an addition funnel, 25 mL of the resin was washed with 250 mL of aqueous 1N sodium hydroxide solution and then with water until the pH stabiliized at approximately 5. The crude product was dissolved in a minimal amount of water, applied to the column and eluted with 150 mL of water. Lyophilization of the eluant afforded 610 mg of material. This was then chromatographed on 23 g of Aldrich silica gel (230–400 mesh, 60 Å) using 10% (v:v) ethanol/methylene chloride to afford 250 mg (24%) of pure material, which was recrystallized from ethanol/hexane to afford 210 mg (20% yield) of a white powder, mp 92° C.; 300 MHz $^1$H NMR(δ, D$_2$O) 4.44 (dddd, $J_{1,2}=5.3$ Hz, $J_{1',2}=11.0$ Hz, $J_{2,3}=9.1$ Hz, $J_{2,F}=50.5$ Hz, 1H, H$_2$), 3.91 (dd, $J_{5,6}=2.6$ Hz, $J_{6,6'}=12.8$ Hz, 1H H$_{6'}$), 3.84 (dd, $J_{5,6'}=2.6$ Hz, $J_{6,6'}=12.8$ Hz, 1H, H$_6'$), 3.57 (dt, $J_{2,3}=J_{3,4}=9.1$ Hz, $J_{3,F}=15.3$ Hz, 1H, H$_3$), 3.43 (t, $J_{3,4}=J_{4,5}=9.1$ Hz, 1H, H$_4$), 3.24 (ddd, $J_{1,2}=5.3$ Hz, $J_{1,1'}=11.0$ Hz, $J_{1,F}=4.1$ Hz, 1H, H$_1$), 2.83–2.61 (m, 2H, N-CH$_2$), 2.50 (ddd, $J_{1',2}=11.0$ Hz, $J_{1,1'}=11.0$ Hz, $J_{1',F}=5.1$ Hz, 1H, H$_{1'}$), 2.29 (dt, $J_{5,6}=J_{5,6'}=2.6$ Hz, $J_{4,5}=9.1$ Hz, 1H, H$_5$) 1.55–1.42(m,2H), 1.31(sextuplet, J=7.0 Hz, 2H) and 0.93 (t, J=7.0 Hz,3H); 101 MHz $^{13}$C NMR (D$_2$O) 92.7 (d, $J_{C2,F}$173.7 Hz, C$_2$), 79.5 (d, $J_{C3,F}=17.0$ Hz, C$_3$), 72.3 (d, $J_{C4,F}=11.6$ Hz, C$_4$), 67.6, 60.1, 55.3 (d, $J_{Cl,F}=25.4$, C$_1$) 54.6, 28.0 and 16.1 ppm;

mass spectrum (m/e) 222 (M+H); and Anal. Calcd. for $C_{10}H_{20}FNO_3$: $C$ (54.27), H (9.13) and N (6.32); Found C (54.54), H (9.42) and N (6.24).

EXAMPLE 13

This example illustrates glycosidase inhibition activity for 1,2-dideoxy-2-fluoronojirimycin (1) and N-butyl-1,2-dideoxy-2-fluoronojirimycin (2). It is contemplated that other N-derivatives will also manifest glycosidase inhibition activity.

The glycosidase inhibition activity is determined by modifying an assay procedure described in Evans et al, Phytochemistry, 22, pp. 768–770 (1983). More particularly, yeast α-glucosidase and almond β-glucosidase activities were measured by the Evans et al method which was modified by assaying activities at pH 7.4 in N-2-hydroxyethylpiperazine-N-2-ethane sulfonic acid (HEPES) buffer, measuring in 96 well microtiter plates, and including 10% DMSO in control and test samples.

The release of p-nitrophenol from the substrate p-nitrophenylglycoside was measured spectrophotometrically in the presence and absence of test compound. Each assay included a known inhibitor of the enzyme as a standard. $IC_{50}$ values were determined for compounds which inhibited the enzymes more than 50% at a 1 millimolar concentration.

α-Glucosidase Inhibition Assay, pH 7.4

To 100 ul 50 mM HEPES buffer, pH 7.4, in a microtiter plate, 20 ul test compound in DMSO (DMSO alone in control) and 40 ul (0.013 units) yeast α-glucosidase (Sigma) in HEPES buffer were added and pre-incubated at room temperature 15 minutes. 40 ul 1.25 mM p-nitro-phenyl-α-D-glucopyranoside (Sigma) in HEPES buffer, as substrate was added and the absorbance change at 405 nm was monitored in a Biotek EIA Autoreader. Absorption change was measured at 15 to 25 minutes (reaction was linear for at least 30 minutes). Each sample was tested in triplicate. $IC_{50}$ values were determined from the linear portion of the log concentration vs percent inhibition curve obtained from a minimum of 3 points. Deoxynojirimycin was used as standard inhibitor.

β-Glucosidase Inhibition Assay pH 7.4

To 100 ul 50 mM HEPES buffer, pH 7.4, in a microtiter plate, 20 ul test compound in DMSO (DMSO alone in control) and 40 ul (0.136 units) β-glucosidase (Sigma) in HEPES buffer were added and pre-incubated at room temperature 15 minutes. 40 ul 1.25 mM p-nitrophenyl-β-D-glucopyranoside in HEPES buffer was added as substrate and the absorbance change at 405 nm was monitored utilizing a Biotek EIA Autoreader. Absorption change was measured at 15 to 25 minutes (reaction is linear for at least 30 minutes). Each sample was tested in triplicate. $IC_{50}$ values were determined from the linear portion of the log concentration vs percent inhibition curve obtained from a minimum of 3 points. Castanospermine was used as standard inhibitor.

pH 4.8

To 100 ul 50 mM sodium citrate buffer, pH 4.8, in a microtiter plate, 20 ul test compound in DMSO (DMSO alone in control) and 20 ul (.017 units) β-glucosidase (Sigma) in citrate buffer were added and pre-incubated at room temperature 15 minutes. 20 ul 2.50 mM p-nitrophenyl-β-D-glucopyranside in citrate buffer was added as substrate and incubated at room temperature 20 minutes (reaction is linear for at least 30 minutes). 50 ul 0.4 M NaOH was added and the absorption change at 405 nm was determined utilizing a Biotek EIA Autoreader. Each sample was tested in triplicate. $IC_{50}$ values were determined from the linear portion of the log concentration vs percent inhibition curve obtained from a minimum of 3 points. Castanospermine was used as standard inhibitor.

TABLE 1

| | | Enzyme and Virus Inhibition Data | | | |
|---|---|---|---|---|---|
| COMPOUND NO. | ALPHA GLUCO SIDASE | BETA GLUCO SIDASE- pH 4.8 | BETA GLUCO SIDASE- pH 7.4 | ALPHA MANNO SIDASE- pH 4.5 | ALPHA MANNO SIDASE- pH 7.4 |
| 1 | 24% @ 1 mM | 6% @ 1 mM | 11% @ 1 mM | 4% @ 1 mM | 19% @ 1 mM |
| | 64% @ 5 mM | 25% @ 5 mM | 25% @ 5 mM | 5% @ 5 mM | 11% @ 5 mM |
| 2 | 8% @ 1 mM | 2% @ 1 mM | 4% @ 1 mM | 3% @ 1 mM | 4% @ 1 mM |
| | 13% @ 5 mM | −6% @ 5 mM | 11% @ 5 mM | 5% @ 5 mM | 12% @ 5 mM |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compound represented by the formula:

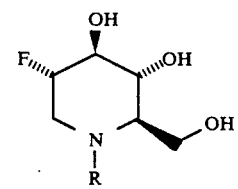

wherein R represents hydrogen, alkyl radicals having from 1 to about 10 carbon atoms, alkenyl radicals having from 2 to about 10 carbon atoms, aryl, alkaryl and aralkyl radicals having from about 6 to about 16 carbon atoms and radicals represented by the formula:

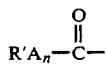

wherein R' represents alkyl radicals, having from about 1 to about 10 carbon atoms, and aryl, aralkyl and alkaryl radicals having from about 6 to about 26 carbon atoms, A represents oxygen, and n is 0 or 1.

2. Compound of claim 1 wherein R represents hydrogen.

3. Compound of claim 1 wherein R represents an alkyl radical having from 1 to about 10 carbon atoms.

4. Compound of claim 1 wherein R represents an alkyl radical having from 1 to about 6 carbon atoms.

5. Compound of claim 1 wherein R represents an alkyl radical having 4 carbon atoms.

6. Compound of claim 1 wherein R is n-butyl.

7. N-butyl-1,2-dideoxy-2-fluroronojirimycin.

8. 1,2-dideoxy-2-fluoronojirimycin.

9. Compound represented by the formula:

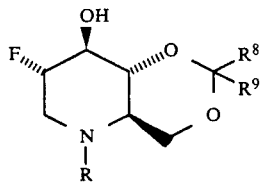

wherein R represents hydrogen, alkyl radicals having from 1 to about 10 carbon atoms, alkenyl radicals having from 2 to about 10 carbon atoms, aryl, aralkyl and alkaryl radials having from about 6 to about 16 carbon atoms and radicals represented by the formula:

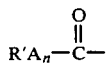

wherein R' represents alkyl radicals, having from 1 to about 10 carbon atoms, and aryl, aralkyl and alkaryl radicals ahving from about 6 to about 26 carbon atoms, A represents oxygen, and n is 0 or 1; and $R^8$ and $R^9$ independently represent hydrogen, alkyl radicals having from 1 to about 10 carbon atoms and aryl radicals.

10. Compound of claim 9 wherein R represents hydrogen.

11. Compound of claim 9 wherein R represents an alkyl radical having from 1 to about 10 carbon atoms.

12. Compound of claim 9 wherein R represents an alkyl radical having from 1 to about 6 carbon atoms.

13. Compound of claim 9 wherein R represents an alkyl radical having 4 carbon atoms.

14. Compound of claim 9 wherein R is n-butyl.

15. Compound of claim 9 wherein R represents a carbobenzoxy radical.

16. Compound of claim 9 wherein R represents a butyryl radical.

17. Composition for inhibiting glycosidase activity comprising a compound of claim 3 and a pharmaceutically acceptable diluent and/or carrier.

18. Composition for inhibiting glycosidase activity comprising a compound of claim 9 and a pharmaceutically acceptable diluent and/or carrier.

19. Method of making a compound of claim 9 comprising reacting an N-protected-2,3 anhydro-4,6-O-protected-1-deoxymannojirimycin with a fluorine source.

* * * * *